US012714771B2

(12) United States Patent
Furuhashi et al.

(10) Patent No.: US 12,714,771 B2
(45) Date of Patent: Aug. 25, 2026

(54) BLOOD PURIFICATION DEVICE

(71) Applicant: Nikkiso Company Limited, Tokyo (JP)

(72) Inventors: Tomohiro Furuhashi, Shizuoka (JP); Hideto Maki, Shizuoka (JP); Ferenc Kazinczi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 843 days.

(21) Appl. No.: 17/417,629

(22) PCT Filed: Nov. 8, 2019

(86) PCT No.: PCT/JP2019/043936
§ 371 (c)(1),
(2) Date: Jun. 23, 2021

(87) PCT Pub. No.: WO2020/137190
PCT Pub. Date: Jul. 2, 2020

(65) Prior Publication Data

US 2022/0111130 A1 Apr. 14, 2022

(30) Foreign Application Priority Data

Dec. 28, 2018 (JP) ................................ 2018-248122

(51) Int. Cl.
*A61M 1/16* (2006.01)
*A61M 1/36* (2006.01)
*A61M 60/279* (2021.01)

(52) U.S. Cl.
CPC ........ *A61M 1/1643* (2014.02); *A61M 1/3621* (2013.01); *A61M 1/3623* (2022.05);
(Continued)

(58) Field of Classification Search
CPC .............. A61M 1/1643; A61M 1/3621; A61M 1/3623; A61M 60/279; A61M 2202/0021;
(Continued)

(56) References Cited

U.S. PATENT DOCUMENTS 7,618,542 B2 11/2009 Okazaki
8,202,241 B2 * 6/2012 Karakama ........... A61M 1/1605
604/4.01
(Continued)

FOREIGN PATENT DOCUMENTS

CN 1688351 A 10/2005
CN 103379926 A 10/2013
(Continued)

OTHER PUBLICATIONS

Japanese Office Action for Application No. 2020-562893, dated Nov. 8, 2022, with English translation, 5 pages.
(Continued)

*Primary Examiner* — Rebecca E Eisenberg
*Assistant Examiner* — Kate Elizabeth Strachan
(74) *Attorney, Agent, or Firm* — Young Basile Hanlon & MacFarlane, P.C.

(57) ABSTRACT

A blood purification device includes a blood circuit for extracorporeally circulating blood of a patient; a liquid supply line for supplying a supply liquid to a blood purifier provided on the blood circuit or to the blood circuit a peristaltic liquid supply pump provided on the blood circuit or on the liquid supply line; a peristaltic waste liquid pump provided on a waste liquid line through which a waste liquid is discharged from the blood purifier; a water balance amount detection unit for detecting a water balance amount of the supply liquid and the waste liquid; and a water balance amount control unit that corrects one or both of pump speeds of the liquid supply pump and the waste liquid pump so that the water balance amount detected by the water balance amount detection unit matches a target water balance amount. The water balance amount control unit is configured to be able to switch between a first correction condition for correcting the pump speed on every water balance amount
(Continued)

detection and a second correction condition for correcting the pump speed based on a plurality of water balance amount detection results.

17 Claims, 4 Drawing Sheets

(52) U.S. Cl.
CPC ... *A61M 60/279* (2021.01); *A61M 2202/0021* (2013.01); *A61M 2202/0413* (2013.01); *A61M 2205/3327* (2013.01); *A61M 2205/3393* (2013.01)

(58) Field of Classification Search
CPC .. A61M 2202/0413; A61M 2205/3327; A61M 2205/3393; A61M 2205/3334; A61M 2205/52; A61M 1/3451
See application file for complete search history.

(56) References Cited

U.S. PATENT DOCUMENTS

| | | | | |
|---|---|---|---|---|
| 9,089,639 | B2 | 7/2015 | Breuel et al. | |
| 2006/0124548 | A1 | 6/2006 | Okazaki | |
| 2011/0257891 | A1* | 10/2011 | Akonur | A61M 1/16 702/19 |
| 2012/0085707 | A1* | 4/2012 | Beiriger | B01D 61/30 210/143 |
| 2012/0193290 | A1* | 8/2012 | Breuel | A61M 1/3451 210/85 |
| 2016/0121037 | A1* | 5/2016 | Golarits | A61M 1/1615 604/67 |
| 2016/0151554 | A1* | 6/2016 | Jansson | G05B 15/02 700/282 |
| 2016/0166748 | A1* | 6/2016 | Meyer | A61M 1/1647 210/646 |
| 2017/0296727 | A1* | 10/2017 | Burbank | A61M 1/165 |
| 2020/0230311 | A1* | 7/2020 | Nimura | A61M 1/36 |

FOREIGN PATENT DOCUMENTS

| | | | | |
|---|---|---|---|---|
| JP | 2007-285830 | A | 11/2007 | |
| JP | 2014-513990 | A | 6/2014 | |
| JP | 2016-87442 | A | 5/2016 | |
| JP | 2016112399 | A * | 6/2016 | A61M 1/1006 |
| WO | 2004/014463 | A1 | 2/2004 | |
| WO | 2017/073732 | A1 | 5/2017 | |

OTHER PUBLICATIONS

International Search Report for Application No. PCT/JP2019/043936, dated Feb. 4, 2020.

European Search Report for Application No. 19901593.4, dated Aug. 12, 2022, 8 pgs.

Chinese Office Action for Application No. 201980086039.0, dated Nov. 29, 2023, with English translation, 16 pgs.

* cited by examiner

BLOOD PURIFICATION DEVICE

CROSS-REFERENCE TO RELATED APPLICATION(S)

This application is a national stage entry of International Application No. PCT/JP2019/043936, filed on Nov. 8, 2019, which claims priority to Japanese Application No. 2018-248122, filed on Dec. 28, 2018, the entire disclosures of which are hereby incorporated by reference.

TECHNICAL FIELD

The invention relates to a blood purification device.

BACKGROUND ART

For blood purification devices used for blood purification treatment, it is important to manage an amount of removed water that is an amount of water removed from blood of a patient.

Patent Document 1 proposes a device that is provided with storage containers for respectively primarily storing a dialysate, a replenishing liquid and a waste liquid from a blood purifier, and a weight scale for measuring weight of the three storage containers all together, and it controls a pump speed (a pump flow rate) of the dialysate, the replenishing liquid or the waste liquid based on the detection result from the weight scale so as to achieve a target removed water amount.

CITATION LIST

Patent Literature

Patent Document 1: WO 2004/014463

SUMMARY OF INVENTION

Technical Problem

In recent years, blood purification treatment tends to be performed at a higher flow rate and it is accordingly desired to further reduce an error of the water balance amount (the amount of removed water). Therefore, it is necessary to precisely correct the pump speed (the pump flow rate) so that the actual water balance amount can be close to the target water balance amount (the target removed water amount).

Particularly at the initial stage of treatment, it is desired that the error of the water balance amount (the amount of removed water) due to manufacturing tolerances or treatment conditions (pressure on the inlet side of the pump, etc.) be promptly corrected. It is because when blood purification treatment is performed at a high flow rate and the error of the water balance amount (the amount of removed water) remains large for a long time, a patient may experience burden such as blood pressure fluctuation. However, if the pump speed correction is carried out too rapidly, the weight may not be measured accurately and the error of the removed water amount may further increase when, e.g., an external disturbance occurs by, e.g., a person colliding with the device.

Therefore, it is an object of the invention to provide a blood purification device that is capable of controlling the water balance amount more precisely.

Solution to Problem

The invention according to variation 1 is a blood purification device, comprising: a blood circuit for extracorporeally circulating blood of a patient; a liquid supply line for supplying a supply liquid to a blood purifier provided on the blood circuit or to the blood circuit; a peristaltic liquid supply pump provided on the blood circuit or on the liquid supply line; a peristaltic waste liquid pump provided on a waste liquid line through which a waste liquid is discharged from the blood purifier; a water balance amount detection unit for detecting a water balance amount of the supply liquid and the waste liquid; and a water balance amount control unit that corrects one or both of pump speeds of the liquid supply pump and the waste liquid pump so that the water balance amount detected by the water balance amount detection unit matches a target water balance amount, wherein the water balance amount control unit is configured to be able to switch between a first correction condition for correcting the pump speed on every water balance amount detection and a second correction condition for correcting the pump speed based on a plurality of water balance amount detection results.

The invention according to variation 2 is the blood purification device according to variation 1 ,wherein time for the water balance amount detection unit to detect the water balance amount under the first correction condition is shorter than time for the water balance amount detection unit to detect the water balance amount under the second correction condition.

The invention according to variation 3 is the blood purification device according to variation 1, wherein the water balance amount control unit performs pump speed correction under the first correction condition at the beginning of treatment and switches to pump speed correction under the second correction condition when a stability determination condition for determining that the water balance amount is stabilized is satisfied.

The invention according to variation 4 is the blood purification device according to variation 1, wherein the water balance amount control unit switches to the pump speed correction under the first correction condition when an instability determination condition for determining that the water balance amount is unstable is satisfied during when performing pump speed correction under the second correction condition.

The invention according to variation 5 is the blood purification device according to variation 4, wherein the instability determination condition comprises a change of a control target value for performing blood purification treatment.

The invention according to variation 6 is the blood purification device according to variation 1, wherein the pump speed correction under the second correction condition is performed using a middle value of the plurality of water balance amount detection results.

The invention according to variation 7 is the blood purification device according to variation 1, wherein the water balance amount detection unit comprises a supply liquid subdivision chamber being provided on the liquid supply line and temporarily storing the supply liquid, a waste liquid subdivision chamber being provided on the waste liquid line and temporarily storing the waste liquid, a weight detection mechanism capable of detecting a total weight of the supply liquid subdivision chamber and the waste liquid subdivision chamber, and a change amount calculation unit for calculating an amount of change in weight detected by the weight detection mechanism, and the water balance amount control unit is configured to correct the pump speed so that the amount of change in the weight calculated by the change amount calculation unit matches an amount of change in weight resulting in the target water balance amount.

The invention according to variation 8 is the blood purification device according to variation 7, wherein the water balance amount control unit is configured to perform the pump speed correction under the first correction condition at the beginning of treatment and switch to the pump speed correction under the second correction condition when the stability determination condition for determining that the water balance amount is stabilized is satisfied, and the stability determination condition is defined as a timing at which the sign of the value of a difference between the amount of change in the weight calculated by the change amount calculation unit and the amount of change in weight resulting in the target water balance amount is reversed from positive to negative or vice versa as compared to the beginning of the first correction condition and an absolute value of the difference becomes not more than a predetermined threshold.

The invention according to variation 9 is the blood purification device according to variation 7, wherein the change amount calculation unit uses weight data measured by the weight detection mechanism at every predetermined time interval being set to shorter than time for the water balance amount detection unit to detect the water balance amount and calculates the amount of change in weight in the detection time by the method of least squares.

The invention according to variation 10 is the blood purification device according to variation 1, wherein the pump speed correction is performed by feedback control under the first correction condition and the second correction condition, and the water balance amount control unit performs the pump speed correction by interpolation or extrapolation at the beginning of treatment and then performs the pump speed correction under the first correction condition.

Advantageous Effects of Invention

According to the invention in variation 1, it is possible to provide a blood purification device that is capable of controlling the water balance amount more precisely.

According to the invention in variation 2, it is possible to perform prompt correction under the first correction condition and to perform correction with higher accuracy under the second correction condition.

According to the invention in variation 3, it is possible to correct the water balance amount efficiently and appropriately since the correction is performed with relatively high frequency before the stability determination condition is satisfied and the correction is performed with relatively low frequency after the stability determination condition is satisfied.

According to the invention in variation 4, it is possible to correct the water balance amount efficiently and appropriately since the correction is performed with relatively low frequency before the instability determination condition is satisfied and the correction is performed with relatively high frequency after the instability determination condition is satisfied.

According to the invention in variation 5, when the control target value is changed, it is possible to promptly correct the water balance amount by judging that the instability determination condition is satisfied, and by switching to correction with high frequency.

According to the invention in variation 6, it is possible to exclude abnormal spikes due to vibration, etc., of the device and to perform correction with higher accuracy under the second correction condition.

According to the invention in variation 7, it is possible to control the water balance amount more precisely by correcting the pump speed using the amount of change in weight detected by the weight detection mechanism.

According to the invention in variation 8, it is possible to accurately determine that the water balance amount is stabilized.

According to the invention in variation 9, it is possible to accurately obtain the amount of change in weight.

According to the invention in variation 10, it is possible to achieve a pump speed close to the target value in a shorter time at the beginning of treatment.

DESCRIPTION OF EMBODIMENT

Embodiment

An embodiment of the invention will be described below in conjunction with the appended drawings.

Figure 1:
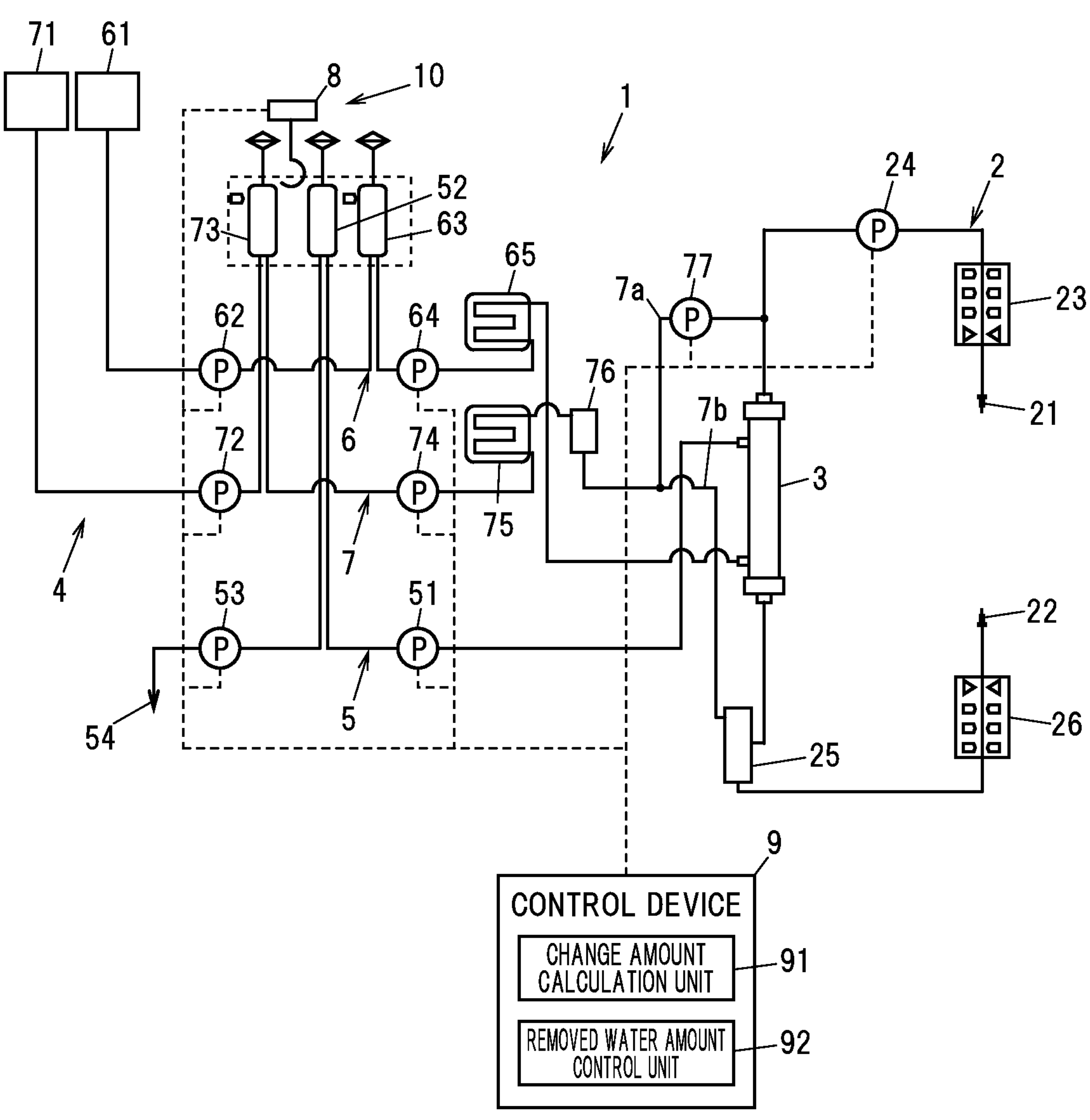
FIG. 1 is a schematic configuration diagram illustrating a blood purification device in an embodiment of the present invention.

FIG. 1 is a schematic configuration diagram illustrating a blood purification device in the present embodiment. As shown in FIG. 1, a blood purification device 1 includes a blood circuit 2 for extracorporeally circulating blood of a patient, liquid supply lines 4 for supplying supply liquids to a blood purifier 3 provided on the blood circuit 2 or to the blood circuit 2, and a waste liquid line 5 through which a waste liquid is discharged from the blood purifier 3.

The blood circuit 2 is composed of, e.g., a flexible tube, etc. An artery-side puncture needle 21 is provided at one end of the blood circuit 2, and a vein-side puncture needle 22 is provided at the other end. In addition, a first air bubble detector 23, a blood pump 24, the blood purifier 3, a gas-liquid separator 25 and a second air bubble detector 26 are sequentially provided on the blood circuit 2 from the artery-side puncture needle 21-side toward the vein-side puncture needle 22-side. The first air bubble detector 23 and the second air bubble detector 26 each have an air bubble detection sensor for detecting air bubbles and a mechanism for clamping (gripping and blocking) the blood circuit 2 when air bubbles are detected.

The blood pump 24 is composed of a peristaltic pump that squeezes the tube to cause blood to flow toward the blood purifier 3. The blood purifier 3 is a device also called a dialyzer and purifies the blood by bringing the blood into contact with a dialysate through a blood purification membrane (not shown). The gas-liquid separator 25 is configured to remove air bubbles and allows passage of only liquid toward the vein-side puncture needle 22-side.

In the present embodiment, the blood purification device 1 has two lines, a dialysate line 6 for supplying a dialysate and a replenishing liquid line 7 for supplying a replenishing liquid, as the liquid supply lines 4 so as to be able to perform various treatments. In this regard, however, the blood purification device 1 may have only one of the dialysate line 6 and the replenishing liquid line 7.

The dialysate line 6 is composed of, e.g., a flexible tube, etc. A dialysate storage bag 61 holding the dialysate is connected to one end of the dialysate line 6. The other end of the dialysate line 6 is connected to a dialysate introduction port of the blood purifier 3. A dialysate transfer pump 62, a dialysate subdivision chamber 63 for temporarily storing the dialysate, a dialysate pump 64, and a dialysate heater 65 are sequentially provided on the dialysate line 6 from the dialysate storage bag 61-side toward the blood purifier 3-side. The dialysate subdivision chamber 63 is one aspect of the supply liquid subdivision chamber of the invention. The dialysate pump 64 is one aspect of the liquid supply pump of the invention.

The dialysate transfer pump 62 and the dialysate pump 64 are each composed of a peristaltic pump that squeezes the tube to cause the dialysate to flow. The dialysate transfer pump 62 is used to transfer the dialysate in the dialysate storage bag 61 to the dialysate subdivision chamber 63. The dialysate pump 64 is used to cause the dialysate in the dialysate subdivision chamber 63 to flow toward the blood purifier 3. Having the dialysate subdivision chamber 63 allows the dialysate storage bag 61 to be replaced without interrupting the treatment. The dialysate heater 65 is to heat the dialysate to an appropriate temperature so that the temperature of the blood to be returned to the patient is not lowered.

The replenishing liquid line 7 is composed of, e.g., a flexible tube, etc. A replenishing liquid storage bag 71 holding the replenishing liquid is connected to one end of the replenishing liquid line 7. A replenishing liquid transfer pump 72, a replenishing liquid subdivision chamber 73 for temporarily storing the replenishing liquid, a replacement pump 74, a replenishing liquid heater 75 and a gas-liquid separator 76 for replenishing liquid are sequentially provided on the replenishing liquid line 7 on the downstream side of the replenishing liquid storage bag 71. The replenishing liquid subdivision chamber 73 is one aspect of the supply liquid subdivision chamber of the invention. The replacement pump 74 is one aspect of the liquid supply pump of the invention.

In addition, the replenishing liquid line 7 branches off on the downstream side of the gas-liquid separator 76 for replenishing liquid, and an end of a pre-fluid replacement line **7*a* as one of the branches of the replenishing liquid line 7 is connected to the blood circuit 2 between the blood purifier 3 and the blood pump 24. A pre-fluid replacement pump 77 is provided on the pre-fluid replacement line 7*a*. An end of a post-fluid replacement line 7*b* as the other branch of the replenishing liquid line 7 is connected to the gas-liquid separator 25 on the blood circuit 2**.

The replenishing liquid transfer pump 72, the replacement pump 74 and the pre-fluid replacement pump 77 are each composed of a peristaltic pump that squeezes the tube to cause the replenishing liquid to flow. The replenishing liquid transfer pump 72 is used to transfer the replenishing liquid in the replenishing liquid storage bag 71 to the replenishing liquid subdivision chamber 73. The replacement pump 74 is used to cause the replenishing liquid in the replenishing liquid subdivision chamber 73 to flow toward the blood circuit 2. The pre-fluid replacement pump 77 is activated when performing "pre-fluid replacement" to supply the replenishing liquid to the blood circuit 2 on the upstream side of the blood purifier 3. When the pre-fluid replacement pump 77 is not activated, the replenishing liquid pumped out by the replacement pump 74 passes through the post-fluid replacement line **7*b*, and "post-fluid replacement" for supplying the replenishing liquid to the blood circuit 2 on the downstream side of the blood purifier 3 (to the gas-liquid separator 25** in this example) is performed.

Having the replenishing liquid subdivision chamber 73 allows the replenishing liquid storage bag 71 to be replaced without interrupting the treatment. The replenishing liquid heater 75 is to heat the replenishing liquid to an appropriate temperature so that the temperature of the blood to be returned to the patient is not lowered. The gas-liquid separator 76 for replenishing liquid is to separate and remove air bubbles from the replenishing liquid.

One end of the waste liquid line 5 is connected to a waste liquid outlet of the blood purifier 3. A waste liquid pump 51, a waste liquid subdivision chamber 52 for temporarily storing the waste liquid and a discharge pump 53 are sequentially provided on the waste liquid line 5 on the downstream side of the blood purifier 3. The other end of the waste liquid line 5 is a waste liquid outlet 54 for discharging the waste liquid to the outside of the device.

The waste liquid pump 51 and the discharge pump 53 are each composed of a peristaltic pump that squeezes the tube to cause the waste liquid to flow. The waste liquid pump 51 is used to send the waste liquid to the waste liquid subdivision chamber 52. The discharge pump 53 is used to discharge the waste liquid in the waste liquid subdivision chamber 52 toward the waste liquid outlet 54.

The blood purification device 1 also has a removed water amount detection unit 10 as a water balance amount detection unit that detects a water balance amount of the supply liquid and the waste liquid. The removed water amount detection unit 10 detects the amount of removed water based on the supplied amount of the supply liquid and the discharged amount of the waste liquid. The removed water amount detection unit 10 has the respective subdivision chambers 63, 73, 52, a load meter 8 as a weight detection mechanism capable of detecting a total weight of the respective subdivision chambers 63, 73, 52, and a change amount calculation unit 91. The amount of removed water here is a water balance amount when the water balance amount of the supply liquid and the waste liquid is negative. In the following description, the case where the water balance amount is negative will be described, and the water balance amount is described as the amount of removed water. However, the invention is also applicable when the water balance amount of the supply liquid and the waste liquid is positive (e.g., when performing fluid replacement).

The load meter 8 is configured to be able to detect a total weight of the dialysate subdivision chamber 63, the replenishing liquid subdivision chamber 73 and the waste liquid subdivision chamber 52. A detection value of the load meter 8 is output to a control device 9.

When the amount of removed water is, e.g., 0 (zero), the supplied amount of the dialysate or the replenishing liquid is equal to the discharged amount of the waste liquid. Therefore, the reduced amount of the dialysate or the replenishing liquid in the dialysate or replenishing liquid subdivision chamber 63 or 73 is equal to the increased amount of the waste liquid in the waste liquid subdivision chamber 52 and the detection value of the load meter 8 does not change temporally. On the other hand, when the amount of removed water is large, the increased amount of the waste liquid in the waste liquid subdivision chamber 52 becomes greater than the reduced amount of the dialysate or the replenishing liquid in the dialysate or replenishing liquid subdivision chamber 63 or 73. Thus, the detection value of the load meter 8 gradually increases. Therefore, it is possible to detect the amount of removed water by detecting a temporal change in the detection value of the load meter 8 (an amount of change in weight).

In the present embodiment, the temporal change in the detection value of the load meter 8, i.e., the amount of change in weight detected by the weight detection mechanism (the amount of change in weight per unit time, i.e., slope) is used as an index of the amount of removed water. Time to measure the load when calculating the amount of change in weight is referred to as detection time. The change amount calculation unit 91 calculates the amount of change in weight in the set detection time. The change amount calculation unit 91 is mounted on the control device 9 and is realized by appropriately combining an arithmetic element such as CPU, a memory, a storage device, a software, and an interface, etc.

The change amount calculation unit 91 preferably uses load data measured by the load meter 8 at every predetermined time interval being set to shorter than the set detection time (time for the removed water amount detection unit 10 to detect the amount of removed water) and calculates the amount of change in (slope of) weight in the detection time by the method of least squares. As a result, it is possible to suppress variation in the load detection value due to pulsation of each pump, allowing for pump speed correction with higher accuracy. The details of the pump speed correction will be described later.

The blood purification device 1 repeats a measurement preparation phase in which the dialysate or the replenishing liquid (e.g., a non-blood liquid) in the storage bag 61 or 71, located upstream of the liquid supply line, is transferred to the subdivision chamber 63 or 73 by the transfer pump 62 or 72 and the waste liquid in the waste liquid subdivision chamber 52 is discharged by the discharge pump 53, and a measurement phase in which the transfer pump 62 or 72 and the discharge pump 53 are stopped and measurement by the load meter 8 is conducted to determine the amount of change in weight. By changing the amount of the dialysate or the replenishing liquid transferred to the subdivision chamber 63 or 73 in the measurement preparation phase, it is possible to appropriately change duration of the measurement phase, i.e., the detection time described above. When, e.g., long detection timeis desired, the amount of the dialysate or the replenishing liquid transferred to the subdivision chamber 63 or 73 in the measurement preparation phase is increased (e.g., a second direction time is longer than a first detection time). In this regard, each pump (the blood pump 24, the dialysate transfer pump 62, the dialysate pump 64, the replenishing liquid transfer pump 72, the replacement pump 74, the pre-fluid replacement pump 77, the waste liquid pump 51 and the discharge pump 53) is controlled by the control device 9.

Pump Speed Correction

The blood purification device 1 in the present embodiment includes a removed water amount control unit 92 as a water balance amount control unit that corrects the pump speed (the pump flow rate) of one or both of the liquid supply pump (the dialysate pump 64 or the replacement pump 74) and the waste liquid pump 51 so that the amount of removed water detected by the removed water amount detection unit 10 matches a target removed water amount. In the present embodiment, the removed water amount control unit 92 is configured to correct the pump speed so that the amount of change in (slope of) weight calculated by the change amount calculation unit 91 matches a target value of the amount of change in (slope of) weight resulting in the target removed water amount. The removed water amount control unit 92 uses feedback control such as Proportional-Intergral-Derivative (PID) control and Proportional-Itegral (PI) control so as to be able to promptly control the amount of removed water so that the amount of change in (slope of) weight becomes close to the target value. The removed water amount control unit 92 is mounted on the control device 9 and is realized by appropriately combining an arithmetic element such as CPU, a memory, a storage device, a software, and an interface, etc.

The pump speeds of the liquid supply pump (the dialysate pump 64 or the replacement pump 74) and the waste liquid outlet 54 may be both corrected, but the control is complicated. Therefore, it is more desirable that the pump speed of one of them be corrected while maintaining the pump speed of the other constant. In addition, when using both the dialysate pump 64 and the replacement pump 74 (when simultaneously performing dialysis treatment and fluid replacement treatment), it should be configured to correct the pump speed of the waste liquid pump 51 to further simplify the control.

Here, causes of the error of the amount of removed water is examined. The causes of the error of the amount of removed water include the following four causes.

(1) Manufacturing variation in the inner diameter of the squeezed portion of the tube (pump segment)

(2) Change of inlet pressures of the pumps (particularly, the waste liquid pump 51) according to treatment conditions (3) Deterioration of the tube (a decrease in restoring force) due to lengthy treatment (4) Load measurement error due to vibration of the device It is not possible to avoid the cause (1) since about ±3% of manufacturing variation in the inner diameter occurs in the tube (pump segment) even with exacting manufacturing tolerances. The cause (2) is due to, e.g., an increase in the amount of removed water, an increase in a filtration rate of the blood purifier 3 caused thereby, which causes an increase in suction resistance of the waste liquid pump 51 (a decrease in pressure on the inlet side of the waste liquid pump 51), resulting in a decrease in the pump flow rate. The cause (3) is due to a decrease in restoring force of the tube (pump segment) and a resulting decrease in the pump flow rate when the treatment is continued for a long time. In recent years, very long treatment such as CRRT (continuous renal replacement therapy) is performed and it is thus not possible to avoid the cause (3), neither, even though depending on the treatment time. The cause (4) is due to an error of the detection value of the load meter 8 caused by a peripheral person or a patient colliding with the device.

The error associated with the causes (1) and (2) among the four causes is desired to be reduced as soon as possible by correcting the pump speed at the beginning of treatment. The error associated with the cause (3) does not require urgent correction and may be corrected while taking time since it is an error that gradually increases with time. The error associated with the cause (4) can be dealt with by increasing the measuring time or by correcting the pump speed using results of multiple measurements, but in this case, it takes time to correct the pump speed.

Based on this, the removed water amount control unit 92 of the invention is configured to be able to switch between the first correction condition for correcting the pump speed with first frequency based on a difference amount between the amount of removed water detected by the removed water amount detection unit 10 and a target removed water amount, and the second correction condition for correcting the pump speed with second frequency less than the first frequency based on the difference amount. In the present embodiment, since the amount of change in (slope of) weight is used as an index of the amount of removed water, the removed water amount control unit 92 is configured to be able to switch between the first correction condition for correcting the pump speed with the first frequency based on a difference amount between the amount of change in weight detected by the removed water amount detection unit 10 and the target removed water amount, and the second correction condition for correcting the pump speed with the second frequency less than the first frequency based on the difference amount.

In more particular, the removed water amount control unit 92 performs the pump speed correction under the first correction condition at the beginning of treatment and switches to the pump speed correction under the second correction condition when a stability determination condition for determining that the water balance amount is stabilized is satisfied.

Under the first correction condition, the correction is performed with high frequency to quickly reduce the error occurred due to the causes (1) and (2). Therefore, under the first correction condition, it is desired to reduce the detection time (time for the removed water amount detection unit 10 to detect the amount of removed water) as much as possible and to repeat the correction in a short time. In the present embodiment, under the first correction condition, the detection time is set to as short as one minute and the pump speed is corrected every time the amount of change in weight is detected. The correction cycle under the first correction condition is shorter than time to detect the amount of removed water once (the detection time) under the second correction condition. By reducing the detection time, it is possible to reduce the amount of the dialysate or the replenishing liquid to fill the subdivision chamber 63 or 73 in the measurement preparation phase and thus to repeat the pump speed correction (feedback control) at shorter time intervals.

Under the second correction condition, in order to reduce the error occurred due to the causes (3) and (4), the detection time (time for the removed water amount detection unit 10 to detect the amount of removed water) is set long and the pump speed is corrected using plural detection results. That is, the time for the removed water amount detection unit 10 to detect the amount of removed water under the first correction condition is shorter than time for the removed water amount detection unit 10 to detect the amount of removed water under the second correction condition.

Under the second correction condition of the present embodiment, the detection time is set to five minutes (time taken for the measurement phase in case of completely filling the subdivision chamber 63, 73 in the measurement preparation phase, i.e., the maximum time for the measurement phase) and the pump speed is corrected using a middle value of three detection results (detection results of the amount of change in weight). That is, the three detection results are compared, the largest value of the amount of change in weight and the smallest value of the amount of change in weight are discarded, and the pump speed is corrected (feedback control) using a remainder middle value of the amount of change in weight. The number of detection results (the number of samples) used under the second correction condition is not limited to three and may be, e.g., five.

Figure 2:
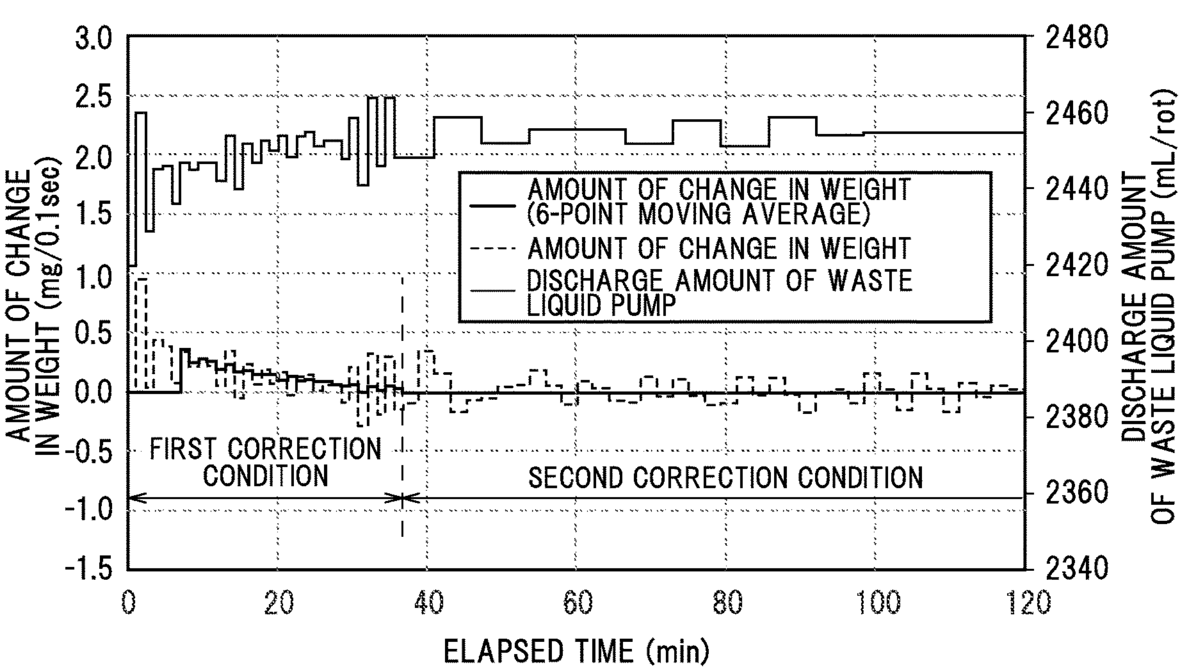
FIG. 2 is a graph showing changes with time in an amount of change in weight, its moving average, and a discharge amount of a waste liquid pump.

As shown in FIG. 2, when the amount of removed water is stabilized and becomes close to the target value, an absolute value of a moving average of a difference between the amount of change in weight and its target value (an average of a predetermined number of detection results) gradually decreases and the sign of the value repeatedly changes between positive and negative. Thus, in the present embodiment, the stability determination condition as a condition for switching from the first correction condition to the second correction condition is defined as a timing at which the sign of the value of a moving average of a difference between the amount of change in weight and its target value is reversed from positive to negative or vice versa as compared to the beginning of the first correction condition and an absolute value thereof becomes not more than a predetermined threshold (e.g., 0.02 mg/sec). However, it is not limited thereto, and the stability determination condition may be a timing at which, e.g., a predetermined time has elapsed from the beginning of the treatment. Although the number of samples at the time of obtaining the moving average is six points in FIG. 2, the number of samples at the time of obtaining the moving average is not limited thereto. However, if the number of samples at the time of obtaining the moving average is too small, it is sometimes not possible to determine that it is sufficiently stable. Therefore, the number of samples at the time of obtaining the moving average is desirably not less than six points. In the present embodiment, the number of samples at the time of obtaining the moving average is twelve points. In this regard, a change in the flow rate of the waste liquid pump 51 is also shown in FIG. 2 for reference. Alternatively, a weighted average or statistical processing may be used instead of the moving average.

Meanwhile, the removed water amount control unit 92 may switch to the pump speed correction under the first correction condition when an instability determination condition for determining that the amount of removed water is unstable is satisfied during when performing the pump speed correction under the second correction condition. The instability determination condition can be a change of a control target value for performing blood purification treatment. When the control target value, i.e., the treatment condition is changed, inlet-side pressure, etc., of the waste liquid pump 51 changes and its discharge amount thus changes, hence, it is desirable to switch to the first correction condition and promptly correct the pump speed. The control target value specifically indicates a target blood flow rate, a target water removal rate, a target dialysate flow rate, and a target replenishing liquid flow rate. The target blood flow rate (a blood pump speed) is a speed of removing blood of a patient and reinfusing the blood, which has passed through the blood purifier 3, to the patient again. The target water removal rate is a speed of extracting a set amount of water from the patient (blood circuit 2). The target dialysate flow rate (a dialysate pump speed) is a speed of sending the dialysate to the blood purifier 3. The target replenishing liquid flow rate (a replacement pump speed) is a speed of sending the replenishing liquid to the blood circuit 2.

Figure 3:
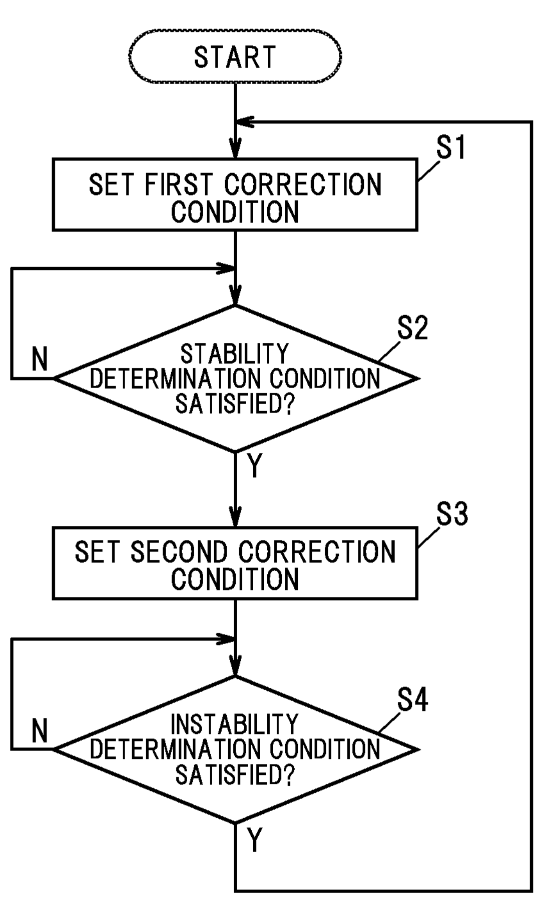
FIG. 3 is a flowchart of control for switching pump speed correction conditions.

FIG. 3 is a flowchart of control for switching the pump speed correction conditions. The control flow in FIG. 3 is initiated at the beginning of treatment, and the control is continued during the treatment. As shown in FIG. 3, firstly, the first correction condition is set at the beginning of treatment in Step S1. Then, in Step S2, it is determined whether the stability determination condition is satisfied. In more particular, in Step S2, it is determined whether the sign of the value of the moving average of the difference between the amount of change in weight and its target value is reversed from positive to negative or vice versa as compared to the beginning of the first correction condition and the absolute value thereof becomes not more than the predetermined threshold (e.g., 0.02 mg/sec). When the determination made in Step 2 is No, the process returns to Step S2 and the first correction condition is maintained. When the determination made in Step 2 is Yes, it is switched to the second correction condition in Step S3.

Then, in Step S4, it is determined whether the instability determination condition is satisfied. In more particular, in Step S4, it is determined whether the treatment condition has been changed. When the determination made in Step 4 is No, the process returns to Step S4 and the second correction condition is maintained. When the determination made in Step 4 is Yes, the process returns to step S1 and it is switched to the first correction condition.

Functions and Effects of the Embodiment

As described above, in the blood purification device 1 according to the present embodiment, the removed water amount control unit 92 is configured to be able to switch between the first correction condition for correcting the pump speed on every water balance amount detection and the second correction condition for correcting the pump speed based on the plural water balance amount detection results.

Thus, by, e.g., setting the first correction condition at the beginning of treatment and correcting the pump speed with high frequency every time the water balance amount is detected, it is possible to promptly reduce the error of the amount of removed water caused by manufacturing tolerances of the tube (pump segment) or the treatment conditions. Furthermore, by switching to the second correction condition after stabilization of the amount of removed water and using the plural detection results of the water balance amount (the amount of change in weight), it is possible to suppress the error due to vibration of the device, etc. In other words, according to the present embodiment, it is possible to realize the blood purification device 1 that is less likely to be affected by an external disturbance occurred by collision with the device, etc., and can control the amount of removed water more precisely while minimizing the error of the amount of removed water even when operating at a high flow rate. The blood purification device 1 can be suitably used particularly when, e.g., performing treatment at a high dialysate or replenishing liquid supply flow rate exceeding 6,000 mL/h, such as when the dialysate or replenishing liquid supply flow rate is not less than 10,000 mL/h.

Another Embodiment

The pump speed is corrected by feedback control (PID control or PI control) under the first correction condition and the second correction condition in the embodiment described above. However, as a third correction condition, pump speed correction by interpolation or extrapolation may be performed prior to the pump speed correction under the first correction condition (i.e., the pump speed correction by feedback control). Pump speed correction by interpolation (linear interpolation), correction using extrapolation such as, e.g., linear extrapolation, or correction using a combination of interpolation and extrapolation is included here.

Under the third correction condition (interpolation or extrapolation), it is possible to achieve the control value close to the target value at an earlier stage than feedback control. Therefore, by performing the pump speed correction under the third correction condition (interpolation or extrapolation) prior to the pump speed correction under the first condition, it is possible to promptly reduce the error of the amount of removed water caused by manufacturing tolerances of the tube (pump segment) or the treatment conditions. By subsequently switching to the pump speed correction by feedback control (the pump speed correction under the first correction condition and the second correction condition), it is possible to control the pump speed with high accuracy.

Figure 4:
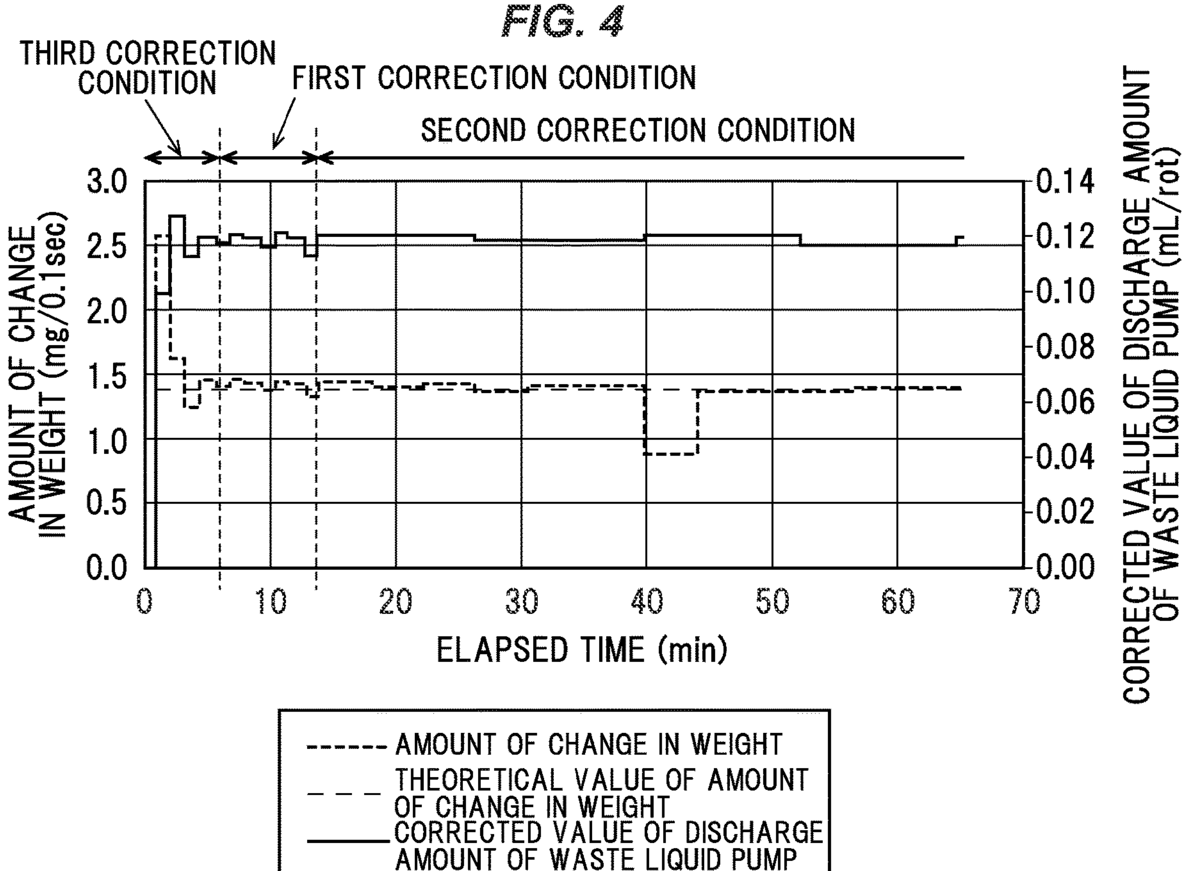
FIG. 4 is a graph showing changes with time in an amount of change in weight and a correction value of the discharge amount of the waste liquid pump in another embodiment.

In more particular, the removed water amount control unit 92 firstly performs the pump speed correction under the third correction condition (interpolation or extrapolation) at the beginning of treatment, as shown in FIG. 4. In the pump speed correction under the third correction condition, it is desirable to correct the pump speed with high frequency, the detection time is set to as short as, e.g., one minute and the pump speed is corrected every time the amount of change in weight is detected, in the same manner as the first correction condition described above. At the time of correcting the pump speed under the third correction condition, the removed water amount control unit 92 decides the correction amount for this time based on the last correction amount, a difference reduced by the last correction amount and a remaining difference so as to satisfy (Last correction amount):(Correction amount for this time)=(Difference reduced by Last correction amount):(Remaining difference), and corrects the pump speed. The "remaining difference" here indicates a difference between the amount of change in weight actually measured after the last correction and the target value, and the "difference reduced by the last correction" indicates a difference of the "remaining difference" before and after the last correction (i.e., a decrease amount of the "remaining difference"). In addition, the last correction amount and the correction amount for this time indicate the correction amount of the pump speed (e.g., of the discharge amount of the waste liquid pump 51).

The removed water amount control unit 92 switches to the pump speed correction under the first correction condition after the pump speed correction under the third correction condition (interpolation or extrapolation). Switching from the third correction condition to the first correction condition may be performed when, i.e., the "remaining difference" becomes not more than a preset threshold value, or when time from the beginning of treatment becomes not less than a preset threshold time, or when the number of corrections becomes not less than a predetermined number. After switching to the first correction condition, the same control as in the above-described embodiment should be performed.

Summary of the Embodiment

Technical ideas understood from the embodiment will be described below citing the reference numerals, etc., used for the embodiment. However, each reference numeral, etc., described below is not intended to limit the constituent elements in the claims to the members, etc., specifically described in the embodiment.

[1] A blood purification device (1), comprising: a blood circuit (2) for extracorporeally circulating blood of a patient; a liquid supply line (4) for supplying a supply liquid to a blood purifier (3) provided on the blood circuit (2) or to the blood circuit (2); a peristaltic liquid supply pump (24, 64, 74) provided on the blood circuit (2) or on the liquid supply line (4); a peristaltic waste liquid pump (51) provided on a waste liquid line (5) through which a waste liquid is discharged from the blood purifier (3); a water balance amount detection unit (10) for detecting a water balance amount of the supply liquid and the waste liquid; and a water balance amount control unit (92) that corrects one or both of pump speeds of the liquid supply pump (24, 64, 74) and the waste liquid pump (51) so that the water balance amount detected by the water balance amount detection unit (10) matches a target water balance amount, wherein the water balance amount control unit (92) is configured to be able to switch between a first correction condition for correcting the pump speed on every water balance amount detection and a second correction condition for correcting the pump speed based on a plurality of water balance amount detection results.

[2] The blood purification device (1) described in [1], wherein time for the water balance amount detection unit (10) to detect the water balance amount under the first correction condition is shorter than time for the water balance amount detection unit (10) to detect the water balance amount under the second correction condition.

[3] The blood purification device (1) described in [1] or [2], wherein the water balance amount control unit (92) performs pump speed correction under the first correction condition at the beginning of treatment and switches to pump speed correction under the second correction condition when a stability determination condition for determining that the water balance amount is stabilized is satisfied.

[4] The blood purification device (1) described in any one of [1] to [3], wherein the water balance amount control unit (92) switches to the pump speed correction under the first correction condition when an instability determination condition for determining that the water balance amount is unstable is satisfied during when performing the pump speed correction under the second correction condition.

[5] The blood purification device (1) described in [4], wherein the instability determination condition comprises a change of a control target value for performing blood purification treatment.

[6] The blood purification device (1) described in any one of [1] to [5], wherein the pump speed correction under the second correction condition is performed using a middle value of the plurality of water balance amount detection results.

[7] The blood purification device (1) described in any one of [1] to [6], wherein the water balance amount detection unit (10) comprises a supply liquid subdivision chamber (63, 73) being provided on the liquid supply line (4) and temporarily storing the supply liquid, a waste liquid subdivision chamber (52) being provided on the waste liquid line (5) and temporarily storing the waste liquid, a weight detection mechanism (8) capable of detecting a total weight of the supply liquid subdivision chamber (63, 73) and the waste liquid subdivision chamber (52), and a change amount calculation unit (91) for calculating an amount of change in weight detected by the weight detection mechanism (8) with the first frequency or the second frequency, and the water balance amount control unit (92) is configured to correct the pump speed so that the amount of change in the weight calculated by the change amount calculation unit (91) matches a target value of an amount of change in weight resulting in the target water balance amount.

[8] The blood purification device (1) described in [7], wherein the water balance amount control unit (92) is configured to perform the pump speed correction under the first correction condition at the beginning of treatment and switch to the pump speed correction under the second correction condition when the stability determination condition for determining that the water balance amount is stabilized is satisfied, and the stability determination condition is defined as a timing at which the sign of the value of a difference between the amount of change in the weight calculated by the change amount calculation unit (91) and the amount of change in weight resulting in the target water balance amount is reversed from positive to negative or vice versa as compared to the beginning of the first correction condition and an absolute value of the difference becomes not more than a predetermined threshold.

[9] The blood purification device (1), described in [7] or [8], wherein, the change amount calculation unit (91) uses weight data measured by the weight detection mechanism (8) at every predetermined time interval being set to shorter than time for the water balance amount detection unit (10) to detect the water balance amount and calculates the amount of change in weight in the detection time by the method of least squares.

[10] The blood purification device (1), described in any one of [1] to [9], wherein the pump speed correction is performed by feedback control under the first correction condition and the second correction condition, and the water balance amount control unit (92) performs the pump speed correction by interpolation or extrapolation at the beginning of treatment and then performs the pump speed correction under the first correction condition.

Although the embodiment of the invention has been described, the invention according to claims is not to be limited the embodiment described above. In addition, all combinations of the features described in the embodiment are not necessary to solve the problem of the invention.

The invention can be appropriately modified and implemented without departing from the gist thereof. For example, although the amount of removed water (the amount of change in weight) is obtained using the load meter 8 in the embodiment described above, it is not limited thereto. The amount of removed water may be obtained using a flow meter for detecting the flow rate of the dialysate, the replenishing liquid or the waste liquid. Furthermore, after measuring the weight of the dialysate storage bag 61 or the replenishing liquid storage bag 71 and the weight of the waste liquid, the amount of removed water may be obtained based on these measurement results. Furthermore, although switching is performed between the two correction conditions, the first correction condition and the second correction condition, or between the first to third correction conditions in the embodiment described above, it may be configured to switch between four or more correction conditions.

REFERENCE SIGNS LIST

- 1: blood purification device
- 2: blood circuit
- 3: blood purifier
- 4: liquid supply line
- 5: waste liquid line
- 51: waste liquid pump
- 52: waste liquid subdivision chamber
- 6: dialysate line
- 63: dialysate subdivision chamber (supply liquid subdivision chamber)
- 64: dialysate pump (liquid supply pump)
- 7: replenishing liquid line

73: replenishing liquid subdivision chamber (supply liquid subdivision chamber)
74: replacement pump (liquid supply pump)
8: load meter (weight detection mechanism)
9: control device
91: change amount calculation unit
92: removed water amount control unit (water balance amount control unit)
10: removed water amount detection unit (water balance amount detection unit)

The invention claimed is:

1. A blood purification device, comprising:

a blood circuit for extracorporeally circulating blood of a patient;

a liquid supply line for supplying a supply liquid, being a non-blood liquid, to a blood purifier provided on the blood circuit or to the blood circuit, wherein the supply liquid is supplied from a storage bag located upstream of the liquid supply line;

a peristaltic liquid supply pump provided on the blood circuit or on the liquid supply line;

a peristaltic waste liquid pump provided on a waste liquid line, the waste liquid line being separate from the blood circuit, through which a waste liquid is discharged from the blood purifier;

a water balance amount detection unit for detecting a water balance amount of the supply liquid and the waste liquid, wherein the water balance amount detection unit comprises:

a supply liquid subdivision chamber, temporarily storing the supply liquid, being provided on the liquid supply line so that the supply liquid is supplied from the storage bag and flows toward the blood purifier, a waste liquid subdivision chamber being provided between a first end and a second end of the waste liquid line downstream of the blood purifier and temporarily storing the waste liquid, a weight detection mechanism capable of detecting a total weight of the supply liquid subdivision chamber and the waste liquid subdivision chamber, and a change amount calculation unit for calculating an amount of change in weight detected by the weight detection mechanism; and a water balance amount control unit that corrects one or both of a pump speed of the peristaltic liquid supply pump and the peristaltic waste liquid pump so that the water balance amount detected by the water balance amount detection unit matches a target water balance amount, wherein the water balance amount control unit is configured to correct the pump speed so that the amount of change in the weight calculated by the change amount calculation unit matches an amount of change in weight resulting in the target water balance amount;

wherein the water balance amount control unit is configured to be able to switch between a first correction condition for correcting the pump speed on every water balance amount detection and a second correction condition for correcting the pump speed based on a plurality of water balance amount detection results, and wherein the water balance amount control unit performs pump speed correction under the first correction condition at a beginning of treatment and switches to pump speed correction under the second correction condition when a stability determination condition for determining that the water balance amount is stabilized is satisfied.

2. The blood purification device according to claim 1, wherein time for the water balance amount detection unit to detect the water balance amount under the first correction condition is shorter than time for the water balance amount detection unit to detect the water balance amount under the second correction condition.

3. The blood purification device according to claim 1, wherein the water balance amount control unit switches to the pump speed correction under the first correction condition when an instability determination condition for determining that the water balance amount is unstable is satisfied during when performing the pump speed correction under the second correction condition.

4. The blood purification device according to claim 3, wherein the instability determination condition comprises a change of a control target value for performing blood purification treatment.

5. The blood purification device according to claim 1, wherein the pump speed correction under the second correction condition is performed using a middle value of the plurality of water balance amount detection results.

6. The blood purification device according to claim 1, wherein the water balance amount control unit is configured to perform the pump speed correction under the first correction condition at the beginning of treatment and switch to the pump speed correction under the second correction condition when the stability determination condition for determining that the water balance amount is stabilized is satisfied, and the stability determination condition is defined as a timing at which a sign of a value of a difference between the amount of change in the weight calculated by the change amount calculation unit and the amount of change in weight resulting in the target water balance amount is reversed from positive to negative or vice versa as compared to the beginning of the first correction condition and an absolute value of the difference becomes not more than a predetermined threshold.

7. The blood purification device according to claim 1, wherein, using weight data measured by the weight detection mechanism at every predetermined time interval that is set to shorter than time for the water balance amount detection unit to detect the water balance amount, the change amount calculation unit calculates the amount of change in weight by a method of least squares.

8. The blood purification device according to claim 1, wherein the pump speed correction is performed by feedback control under the first correction condition and the second correction condition, and the water balance amount control unit performs the pump speed correction by interpolation or extrapolation at the beginning of treatment and then performs the pump speed correction under the first correction condition.

9. The blood purification device according to claim 1, further comprising:

a third correction condition that occurs before the first correction condition and the second correction condition.

10. The blood purification device according to claim 1, further comprising:

feedback control that corrects the pump speed under the first correction condition and the second correction condition.

11. The blood purification device of claim 10, wherein the feedback control corrects the pump speed with Proportional-Integral-Derivative (PID) control or Proportional-Integral (PI) control.

12. The blood purification device of claim 1, wherein the pump speed is an error caused by manufacturing variation in an inner diameter of a squeezed portion of a tube or a change of inlet pressures of the peristaltic liquid supply pump or the peristaltic waste liquid pump according to treatment conditions.

13. The blood purification device of claim 12, wherein the first correction condition is configured to correct the pump speed for the error caused by the manufacturing variation or the change of inlet pressures.

14. The blood purification device of claim 1, wherein the supply liquid subdivision chamber comprises: a dialysate subdivision chamber connected to a dialysate storage that is configured as the storage bag, wherein the dialysate subdivision chamber temporarily stores dialysate from the dialysate storage bag.

15. The blood purification device of claim 1, wherein the liquid supply line comprises a replenishing liquid line that is connected to the blood circuit between the blood purifier and the peristaltic liquid supply pump.

16. The blood purification device of claim 1, wherein the supply liquid subdivision chamber comprises a replenishing liquid subdivision chamber connected to a replenishing liquid storage bag that is configured as the storage bag, wherein the replenishing liquid subdivision chamber temporarily stores a replenishing liquid from the replenishing liquid storage bag.

17. The blood purification device of claim 1, wherein, under the first correction condition, a detection time for a removed water amount detection unit to detect an amount of removed water is set to a first detection time; and wherein, under the second correction condition, the detection time for the removed water amount detection unit to detect the amount of removed water is set to a second detection time that is longer than the first detection time.

* * * * *